United States Patent
Steinhardt et al.

(10) Patent No.: US 7,204,850 B2
(45) Date of Patent: Apr. 17, 2007

(54) AUDITORY OSSICLES PROSTHESIS WITH BALL-AND-SOCKET JOINT

(75) Inventors: Uwe Steinhardt, Hirrlingen (DE); Daniel F. àWengen, Binningen (CH)

(73) Assignee: Heinz Kurz GmbH Medizintechnik, Dusslingen (DE)

( * ) Notice: Subject to any disclaimer, the term of this patent is extended or adjusted under 35 U.S.C. 154(b) by 0 days.

(21) Appl. No.: 10/886,361

(22) Filed: Jul. 7, 2004

(65) Prior Publication Data
US 2005/0027357 A1    Feb. 3, 2005

(30) Foreign Application Priority Data
Jul. 10, 2003    (DE)  ............. 203 10 609 U

(51) Int. Cl.
*A61F 2/18*    (2006.01)
*H04R 25/00*    (2006.01)
(52) U.S. Cl. ........................ 623/10; 600/25
(58) Field of Classification Search ............ 623/10, 623/11.11; 600/25; 607/55–57
See application file for complete search history.

(56) References Cited

U.S. PATENT DOCUMENTS

| | | | | |
|---|---|---|---|---|
| 4,601,723 A * | 7/1986 | McGrew | ............... | 623/10 |
| 5,476,479 A * | 12/1995 | Green et al. | ............... | 606/205 |
| 5,522,839 A * | 6/1996 | Pilling | ............... | 606/207 |
| 5,935,167 A * | 8/1999 | a Wengen | ............... | 623/10 |
| 5,975,363 A * | 11/1999 | Haycock | ............... | 222/103 |
| 6,390,970 B1 | 5/2002 | Mueller | | |
| 6,482,144 B1 * | 11/2002 | Muller | ............... | 600/25 |
| 6,540,661 B1 * | 4/2003 | Muller | ............... | 600/25 |
| 6,547,715 B1 * | 4/2003 | Muller et al. | ............... | 600/25 |
| 2002/0045939 A1 * | 4/2002 | Kurz | ............... | 623/10 |
| 2004/0064183 A1 | 4/2004 | Wengen et al. | | |

FOREIGN PATENT DOCUMENTS

| | | |
|---|---|---|
| DE | 199 15 684 A1 | 11/2000 |
| DE | 200 14 659 U1 | 1/2001 |
| DE | 202 12 771 U1 | 12/2002 |
| FR | 2 675 372 | 10/1992 |

* cited by examiner

*Primary Examiner*—David J. Isabella
(74) *Attorney, Agent, or Firm*—Michael J. Striker

(57) ABSTRACT

An auditory ossicles prosthesis mountable with its one end on a hammer grip of a human auditory ossicies chain and with its another end on a raising bracket of the human auditory ossicles chain or insertable directly into an inner ear, wherein the auditory ossicles prosthesis has a prosthesis element, and an at least one joint integrated in the prosthesis element.

8 Claims, 2 Drawing Sheets

AUDITORY OSSICLES PROSTHESIS WITH BALL-AND-SOCKET JOINT

BACKGROUND OF THE INVENTION

The present invention relates to an auditory ossicles prosthesis, which is mounted with its one end on a hammer grip of a human auditory ossicles chain, and with its other end is mounted on a rising bracket of the human auditory ossicles chain or directly introduced into an inner ear.

Auditory ossicles prostheses are used to transmit the sound from an ear drum to an inner ear in the case of completely or partially failing or damaged auditory ossicles of the human middle ear. The auditory ossicles prosthesis has two ends, wherein depending on the concrete conditions one end of the auditory ossicles prosthesis is mounted for example on the hammer grip of the human auditory ossicles chain, and the other end of the auditory ossicles prosthesis is for example mounted on the rising bracket of the human auditory ossicles chain, or is directly introduced into the inner ear.

Since the anatomic peculiarities of the ear, such as for example the position, the shape, and the size of the raising bracket, the hammer and the ear drum vary, and since after an operation for insertion of the auditory ossicles prosthesis changes can occur in the bone and cartilage structure, it is advantageous when the auditory ossicles prosthesis is not rigid, but instead has a certain flexibility. For obtaining such a flexibility, various mounting devices and coupling devices are proposed for auditory ossicles, which have elastic parts and/or joints.

SUMMARY OF THE INVENTION

Accordingly, it is an object of the present invention to provide an auditory ossicles prosthesis which is a further improvement of the existing prostheses.

In particular, it is an object of the present invention to provide an auditory ossicles prosthesis in which no separate mounting devices or coupling devices must be provided, to obtain the required flexibility, but instead the prosthesis itself possess the flexibility.

In keeping with these objects and with others which will become apparent hereinafter, one feature of the present invention resides, briefly stated, in an auditory ossicles prosthesis mountable with its one end on a hammer grip of a human auditory ossicles chain and with its another end on a raising bracket of the human auditory ossicles chain or insertable directly into an inner ear, wherein the auditory ossicles prosthesis includes a prosthesis element, and an at least one joint integrated in said prosthesis element.

The inventive auditory ossicles prosthesis has at least one integrated joint, to provide the required flexibility. Therefore the auditory ossicles prosthesis is movable itself and does not require any special mounting and coupling devices to guarantee the required flexibility or movability.

In accordance with a preferable embodiment of the present invention, the joint is a ball-and-socket joint which is movable in several directions. When several ball-end-socket joints, for example three ball-end-socket joints are arranged one behind the other, an approximately any movable clearance space of the auditory ossicles prosthesis is provided, both with respect to the direction and the longitudinal extension.

The ball-and-socket joint can include for example a ball which is mounted on a rod and cooperates with a U-shaped trough part formed with openings for improved holding of the ball in the longitudinal side walls.

The auditory ossicles prosthesis must be mounted at its both ends. For example the mounting on the one hand is performed on the hammer grip of the human auditory ossicles chain and mounting on the other hand is performed on the rising bracket of the human auditory ossicles chain or directly in the inner ear.

In accordance with a preferable embodiment of the present invention, for mounting of the inventive auditory ossicles prosthesis on the hammer grip or on the rising bracket, a clip is provided on the corresponding end. For the mounting, it is fitted over the hammer grip or the rising bracket. The clip can be provided with spring tongs arranged on a V-shaped or U-shaped fashion, for the clipping in.

For improving the hold of the clip, the contact points of the clip with the hammer grip or the raising bracket are roughened in accordance with a preferable embodiment. For facilitating the mounting of the clip during the insertion of the prosthesis, the clip can be provided with a holding grip, for example in form of an elongated web.

In accordance with another embodiment of the present invention, for mounting the auditory ossicles prosthesis in the inner ear, instead of the clip preferably a plunger is utilized.

All components of the auditory ossicles prosthesis must be composed of a biocompatible material, to avoid the rejection reactions. As the materials for auditory ossicles prosthesis it is possible to use for example titanium, titanium alloys or nitinol (NiTi).

The novel features which are considered as characteristic for the present invention are set forth in particular in the appended claims. The invention itself, however, both as to its construction and its method of operation, together with additional objects and advantages thereof, will be best understood from the following description of specific embodiments when read in connection with the accompanying drawings.

DESCRIPTION OF THE PREFERRED EMBODIMENTS

Figure 1:
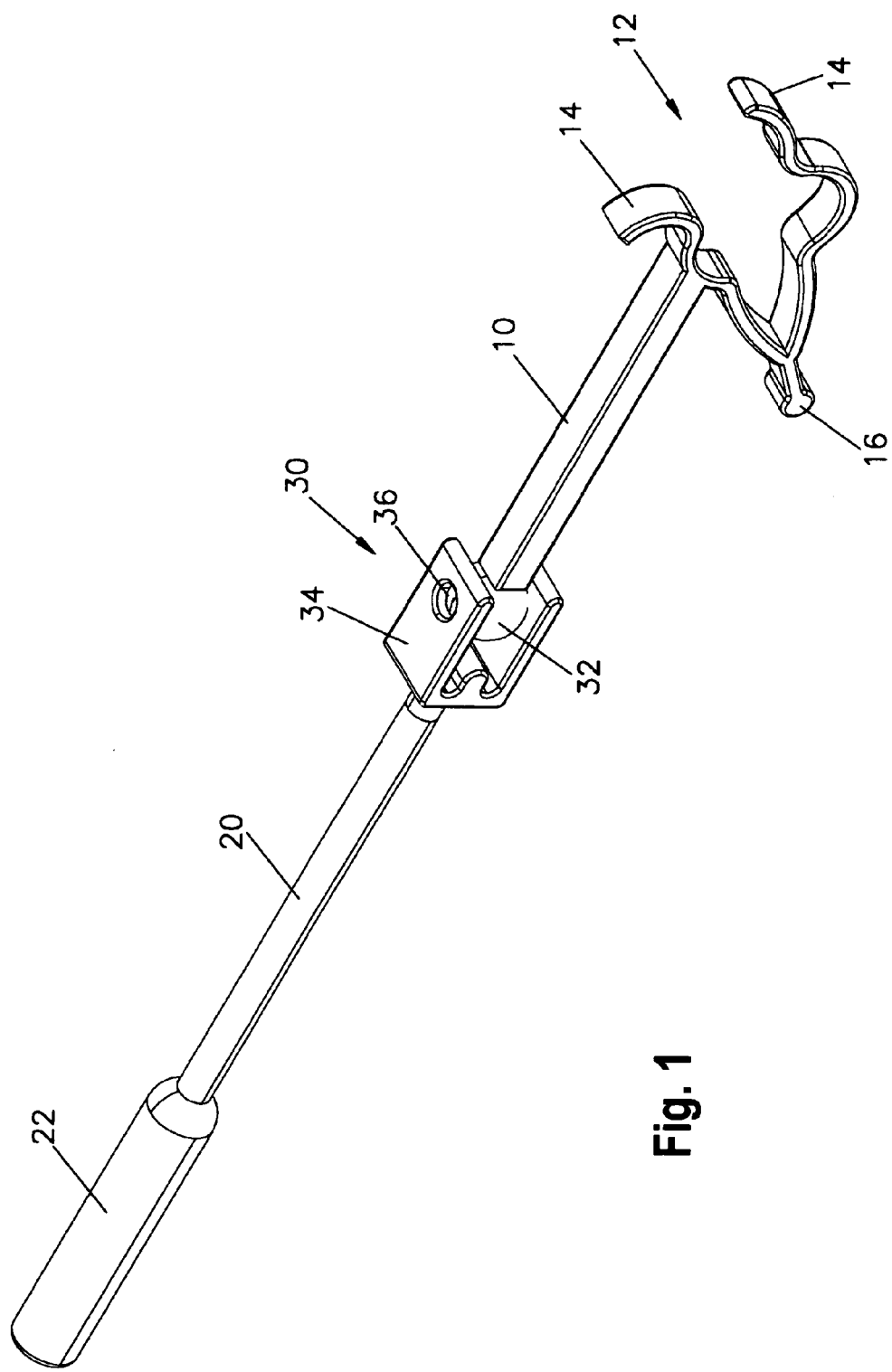
FIG. 1 is a perspective view of an auditory ossicles prosthesis which is formed in accordance with one embodiment of the present invention.

FIG. 1 is a perspective view showing a first embodiment of an auditory ossicles prosthesis which is formed in accordance with the present invention.

The auditory ossicles prosthesis which is composed in this embodiment of two parts, namely a first rod 10 and a second rod 20, which are movably connected with one another through a joint 30.

The first rod 20 at its end is provided with a first clip 12, with which it can be mounted on a not shown hammer grip of the human auditory ossicles chain. The clip 12 in this embodiment has two movable V-shaped spring tongs 14, which can be fitted over the hammer grip. One end of the first clip 12 is formed with the shape of a web as a holding grip 16. Therefore the clip 12, during insertion into an ear, can be easily held on its holding grip 16.

On its opposite end the first rod 10 has a ball 32. This ball serves as a ball of a ball-and-socket joint which is used here for connection of the both rods with one another. The ball is supported on a trough 34. The trough 34 is connected with the second rod 20. In the shown embodiment the trough 34 is U-shaped. It is provided with openings 36 on its longitudinal side walls, to ensure definite support for the ball 32.

The second rod 20, on its opposite end, is provided in this embodiment with a plunger 22. The auditory ossicles prosthesis can be mounted with this plunger directly in the inner ear.

Figure 2:
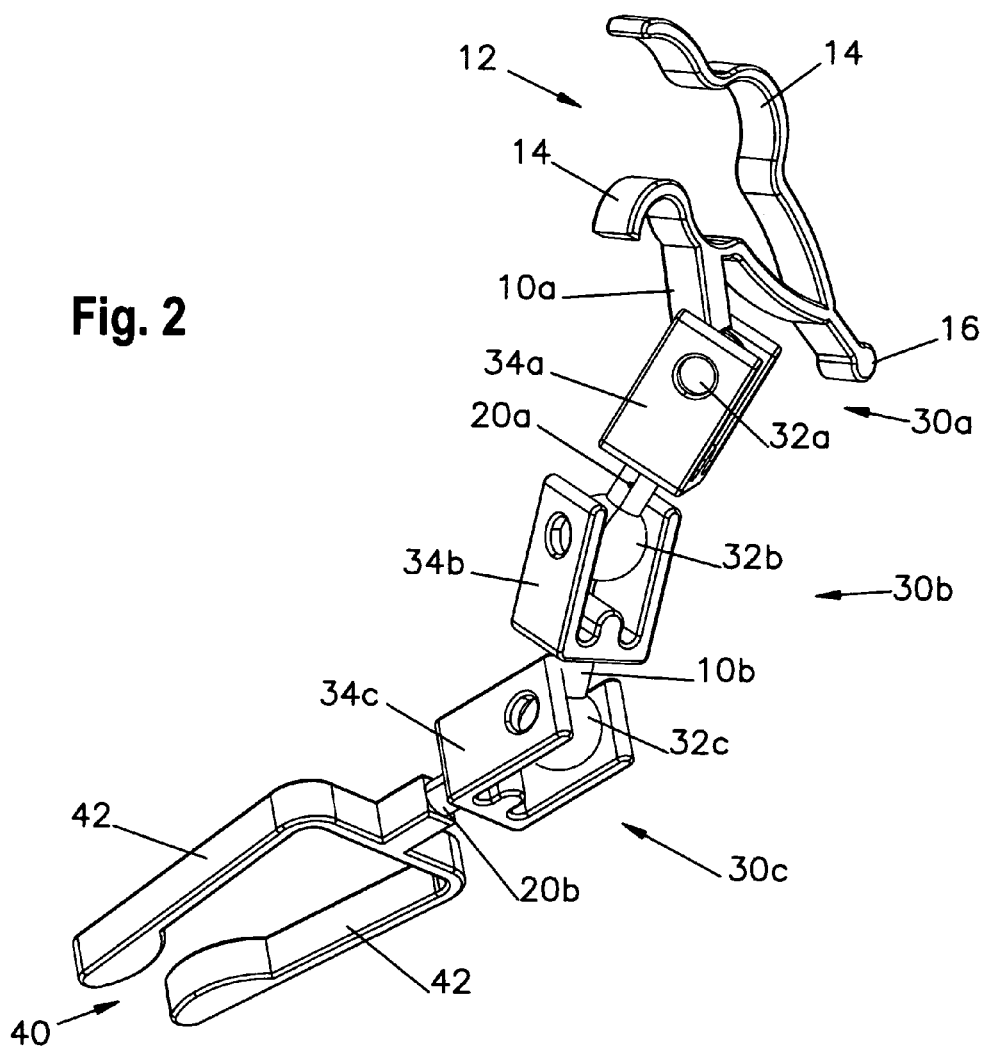
FIG. 2 is a perspective view of an auditory ossicles prosthesis formed in accordance with another embodiment of the present invention.

FIG. 2 shows in a perspective view a second embodiment of the inventive auditory ossicles prosthesis. In this embodiment of the auditory ossicies prostheses, the first and second rods are significantly shortened, since in this case they are connected with one another through three joints 30*a*, 30*b*, 30*c* located one behind the other. Therefore the auditory ossicles prosthesis includes two first rods 10*a*, 10*b* and two second rods 20*a*, 20*b*.

This connection through several joints which are arranged one behind the other provides a flexible orientation and position adjustment of the auditory ossicles prosthesis. However, the rods must be correspondingly shortened so that the prosthesis can be adapted to the inner ear. The joints 30*a*, 30*b*, 30*c* are provided with balls 32*a*, 32*b*, 32*c* and troughs 34*a*, 34*b*, 34*c*, similarly to the joint shown in FIG. 1.

In this embodiment the auditory ossicles prosthesis on its one end has the first clip 12 for mounting on the hammer grip of the human auditory ossicles chain. On its other end it has a second clip 40 which in this case is provided for mounting on the raising bracket of the human auditory ossicles chain. In this embodiment it is composed of two spring tongs 42 which are connected with one another in a U-shaped fashion.

It will be understood that each of the elements described above, or two or more together, may also find a useful application in other types of constructions differing from the types described above.

While the invention has been illustrated and described as embodied in a auditory ossicles prosthesis with ball-end-socket joint, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims.

The invention claimed is:

1. An auditory ossicles prosthesis comprising a plurality of ball-and-socket joints connected in series and terminating in opposite ends forming a prosthesis element configured to be mountable between a hammer grip of a human auditory ossicles chain and a raising bracket of the human auditory ossicles chain or insertable directly into an inner ear; and a clip having V-shaped spring tongs configured to be coupled to at least one end of the prosthesis element for attaching the prosthesis element to at least one of the hammer grip or raising bracket.

2. An auditory ossicles prosthesis as defined in claim 1, wherein each of said ball-and-socket joints has a ball which is mounted on a rod and is supported in a U-shaped trough part.

3. An auditory ossicles prosthesis as defined in claim 2, wherein said U-shaped trough part has longitudinal walls provided with openings, in which said ball is supported.

4. An auditory ossicles prosthesis as defined in claim 1 wherein said clip has contact points for mounting on a hammer grip or on a rising bracket, said contact points being roughened.

5. An auditory ossicles prosthesis as defined in claim 1, wherein said clip is provided with a holding grip.

6. An auditory ossicles prosthesis as defined in claim 1, wherein said prosthesis element is provided with a plunger for mounting directly in an inner ear.

7. An auditory ossicles prosthesis as defined in claim 1, wherein said prosthesis element and said joints are composed of a material selected from the group consisting of titanium, a titanium alloy, and a nitinol.

8. An auditory ossicles prosthesis comprising a plurality of ball-and-socket joints connected in series and terminating in opposite ends forming a prosthesis element configured to be mountable between a hammer grip of a human auditory ossicles chain and a raising bracket of the human auditory ossicles chain or insertable directly into an inner ear; and clip having V-shaped spring tongs configured to be coupled to at least one end of the prosthesis element for attaching the prosthesis element to at least one of the hammer grip or raising bracket, said plurality of said ball-and-socket joints including two end ball-and-socket joints and a ball-and-socket joint located between said end ball-and-socket joints.

* * * * *